(12) United States Patent
Black et al.

(10) Patent No.: US 8,152,806 B2
(45) Date of Patent: Apr. 10, 2012

(54) MONOPOLAR ELECTROSURGICAL INSTRUMENT

(75) Inventors: William B. Black, Stone Mountain, GA (US); Norman M. Black, III, Atlanta, GA (US)

(73) Assignee: Black & Black Surgical, Inc., Tucker, GA (US)

( * ) Notice: Subject to any disclaimer, the term of this patent is extended or adjusted under 35 U.S.C. 154(b) by 877 days.

(21) Appl. No.: 12/283,181

(22) Filed: Sep. 11, 2008

(65) Prior Publication Data

US 2010/0063502 A1 Mar. 11, 2010

(51) Int. Cl.
*A61B 18/14* (2006.01)

(52) U.S. Cl. ........................................ 606/52

(58) Field of Classification Search .............. 606/42, 606/49, 51, 52
See application file for complete search history.

(56) References Cited

U.S. PATENT DOCUMENTS

| 3,100,489 | A | * | 8/1963 | Bagley | 606/42 |
| 4,041,952 | A | * | 8/1977 | Morrison et al. | 606/42 |
| 4,492,231 | A | * | 1/1985 | Auth | 606/42 |
| 5,122,139 | A | * | 6/1992 | Sutter | 606/51 |
| 2005/0240177 | A1 | * | 10/2005 | Tabermejo et al. | 606/42 |

FOREIGN PATENT DOCUMENTS

| DE | 3427946 | * | 11/1985 | 606/51 |
| DE | 3427947 | * | 1/1986 | 606/51 |

OTHER PUBLICATIONS

Achieving a Predictable 24-Hour Return to Normal Activities after Breast Augmentation: Part II. Patient Preparation, Refined Surgical Techniques, and Instrumentation—John B. Tebbetts, M.D.

* cited by examiner

*Primary Examiner* — Lee Cohen
(74) *Attorney, Agent, or Firm* — Rodgers & Rodgers

(57) ABSTRACT

A monopolar electrosurgical instrument including a pair of diverging shanks with a pair of uninsulated tips formed respectively on the distal ends thereof, a housing secured to one of the shanks and having a button disposed therein, a metal wire extending adjacent the one shank so that depression of the button bends the metal rod to energize the instrument.

7 Claims, 1 Drawing Sheet

MONOPOLAR ELECTROSURGICAL INSTRUMENT

BACKGROUND OF THE INVENTION

Historically, electrosurgical forceps have had two shanks, and one variation had two opposing pads on the inside of the forceps shanks that made contact when the forceps tips were pressed together. Another version included a cup on the inside of one shank and a pin on the inside of the other shank. Both of these types of forceps failed because, during surgery, the switch was inside the patient's body and any fluid entering the switch caused an arc to occur which resulted in the patient being burned. Due to these shortcomings, the original monopolar instruments were withdrawn from the market and the only type of monopolar forceps that remained was an instrument with a foot-activated switch by which the problem of arcing is solved, but the surgeon loses tactile feel and control which naturally is undesirable.

In bipolar electrosurgery, both the active electrode and return electrode functions are located at the surgery site wherein the two shanks of the forceps perform the active and return electrode functions. Bipolar electrosurgery uses a low current and is used on very delicate and precise surgeries such as around the eye, female sterilization and other surgeries wherein minimal tissue damage is desired. The coagulation takes place between the tips of the forceps wherein one side of the forceps is active and the other side is the ground.

Monopolar electrosurgery is the most commonly used method of electrosurgery and is versatile and effective wherein the active electrode is the instrument disposed at the surgical site and the return electrode is located somewhere else on the patient's body in the form of a flat grounding plate. Current passes through the patient as it completes the circuit from the active electrode to the patient return electrode and monopolar instruments use more electrical power than bipolar instruments and usually coagulate larger areas.

BRIEF SUMMARY OF THE INVENTION

An electrosurgical monopolar instrument, more particularly surgical forceps, includes a pair of shanks extending from a base element in a diverging manner. The shanks are insulated with the tips, remote from the base, uninsulated and pointed with small serrations formed therein. An insulated hand switch is attached to one of the shanks and includes a housing secured to the shank with a button disposed therein and further includes a pair of laterally extending resilient arms. An energized metal wire extends along the associated shank adjacent the switch such that manipulation of the shanks inwardly causes the button to bend the metal rod into contact with the metal shank to complete the electrical circuit and energize the instrument for the purpose of performing the desired surgical procedure.

DETAILED DESCRIPTION OF THE INVENTION

Figure 1:
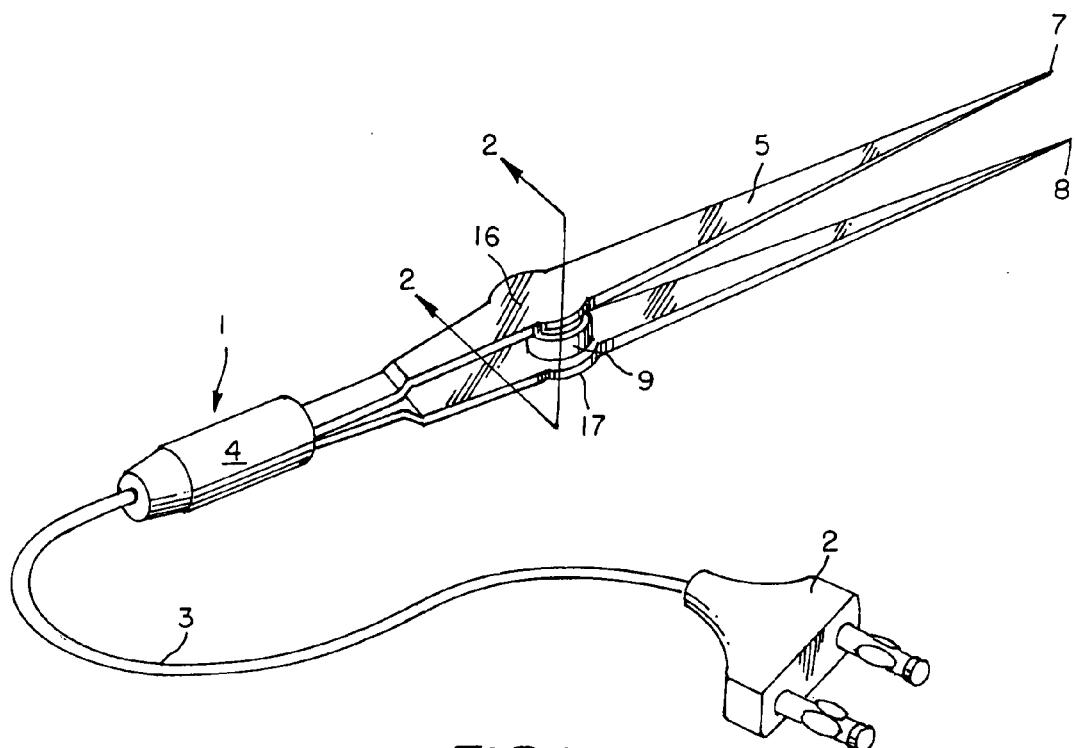
FIG. 1 is a perspective view of the electrosurgical monopolar instrument according to this invention.

In the drawings, and with particular reference to FIG. 1, the monopolar electrosurgical instrument, according to this invention, is shown and is generally indicated by the numeral 1. Instrument 1 includes two-pronged plug 2 which is adapted to be plugged into an electrosurgical unit (ESU) which is commonly called an electrosurgical generator. Cable 3 extends from plug 2 and terminates in base 4 so as to energize instrument 1, in known manner. Autoclavable instrument 1 is made of stainless steel and includes diverging shanks 5 and 6 which are insulated to prevent undesirable current leakage. Tips 7 and 8 are formed on the ends of shanks 5 and 6, respectively, and are pointed with small serrations formed on the inside surfaces of the tips to allow for the grasping, coagulation and dissecting of tissue. Tips 7 and 8 are uninsulated a distance of approximately 12 mm from the ends thereof to accomplish the coagulation and dissection operations.

According to this invention and as shown in the drawings, hand switch 9 is secured on the inside of shank 6 and is sealed to prevent current leakage from the switch as well as liquid entry into the switch. Hand switch 9 includes modified V-shaped button 10 which is disposed within housing 11 and includes outwardly extending resilient arms 12 and 13. Tabs 14 and 15 are integrally formed, respectively, on the outer ends of arms 12 and 13 and are disposed in cavities formed in housing 11. Enlarged portions 16 and 17 are formed, respectively, on shanks 5 and 6 and act as finger pads to make it easier for the surgeon to manipulate the forceps. To complete the basic elements of the forceps, wire 18 is electronically connected, in a conventional manner, to base 4 with metal contact 19 secured on the free end thereof.

Figure 2:
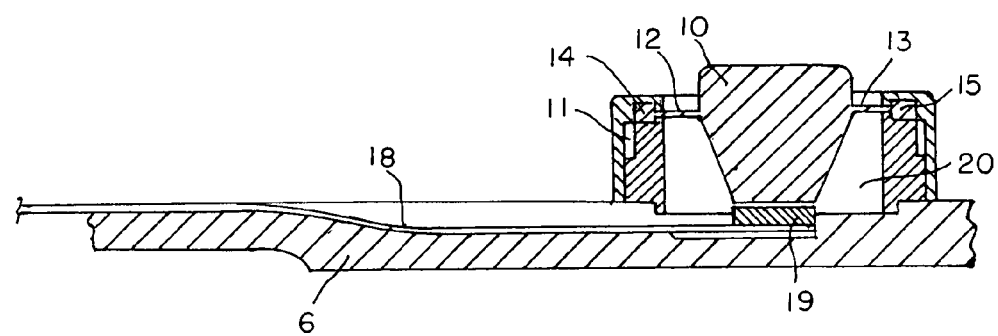
FIG. 2 is a cross-sectional view taken along the line 2-2 in FIG. 1.
Figure 3:
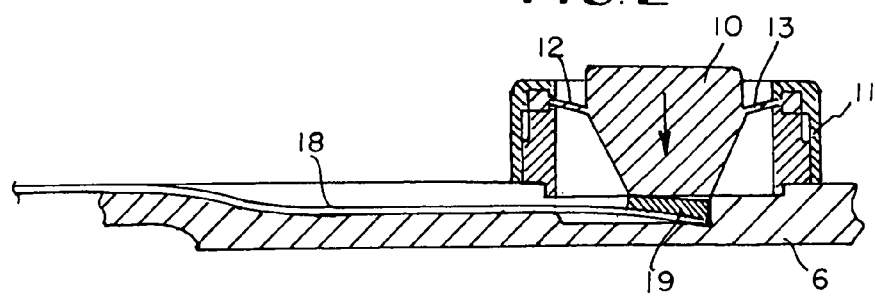
FIG. 3 is a view similar to FIG. 2 showing the instrument switch is in an activated condition.

In operation, hand switch 9 is activated when shanks 5 and 6 are pressed together which causes shank 5 to come into contact with button 10 so as to flex resilient arms 12 and 13 downwardly into open space 20 of housing 11. This causes button 10 to come into metal contact with contact 19 and thereby bend wire 18 downwardly. When the end of wire 18 ultimately comes into contact with metal shank 6, the electrical circuit is complete thereby causing tips 7 and 8 to become energized for the purpose of completing the desired surgical procedure. When pressure on shanks 5 and 6 is released, the resiliency of arms 12 and 13 causes button 10 to spring upwardly from the position shown in FIG. 3 into the position shown in FIG. 2.

Therefore, by this invention, a monopolar electrosurgical instrument is provided having a hand switch which is sealed to eliminate the problem of electrical arcing. The switch can be placed on either the inside or outside of the instrument shank and is activated when button 10 is depressed either by closing shanks 5 and 6, as shown in the drawings, or by depressing button 10 using the surgeon's hand or finger, if button 10 is disposed on the outside of the associated shank.

In summary, this invention combines monopolar forceps with a button switch into one instrument and allows for easy dissection of breast and other tissue to create a pocket and, with the same instrument, allows for coagulation of bleeding vessels to reduce undesirable blood loss. The use of one instrument reduces operating time and enhances the long term results of a particular procedure.

The invention claimed is:

1. A monopolar electrosurgical instrument comprising a pair of diverging shanks extending from a base, said shanks terminating in distal ends, a pair of pointed tips formed respectively on said distal ends of said shanks, a housing secured to one of said shanks intermediate said base and said distal end, a button disposed in said housing, a pair of arms extending outwardly from said button, said arms comprising ends, a pair of tabs integrally formed respectively on said ends of said arms, a pair of cavities formed in said housing, said tabs being disposed respectively in said cavities, a metal wire adapted to be connected to a source of power and extending adjacent said one shank, and said metal wire being disposed between said one shank and said button.

2. An instrument according to claim 1 wherein an open space is formed in said housing and wherein said arms extend into said open space when said shanks are closed together.

3. An instrument according to claim 1 wherein said arms are resilient.

4. An instrument according to claim 1 wherein said shanks are enlarged respectively intermediate said base and said distal ends.

5. An instrument according to claim 1 wherein said metal wire comprises an end and a contact is secured on said end of said metal wire opposite said button.

6. An instrument according to claim 1 wherein said housing is disposed substantially midway between said base and said distal end.

7. An instrument according to claim 6 wherein said one shank comprises an inner surface and said housing is secured on said inner surface of said one shank.

* * * * *